United States Patent [19]

Takano et al.

[11] Patent Number: 5,087,566
[45] Date of Patent: Feb. 11, 1992

[54] PROCESS FOR PRODUCING L-THREONINE

[75] Inventors: Junichi Takano; Satoru Furukawa, both of Hofu; Toshihide Nakanishi, Ube, all of Japan

[73] Assignee: Kyowa Hakko Kogyo., Ltd., Tokyo, Japan

[21] Appl. No.: 428,947

[22] Filed: Oct. 30, 1989

[30] Foreign Application Priority Data

Nov. 10, 1988 [JP] Japan .................................. 63-284386

[51] Int. Cl.⁵ .......................... C12P 13/08; C12N 1/20; C12N 15/00; C12N 1/38
[52] U.S. Cl. .................................. 435/115; 435/252.8; 435/172.1; 435/244; 435/849
[58] Field of Search ............ 435/115, 244, 849, 252.8, 435/172.1

[56] References Cited

U.S. PATENT DOCUMENTS 3,647,628  3/1972  Nakayama ............................ 435/115

FOREIGN PATENT DOCUMENTS 237819  3/1987  European Pat. Off. ............ 435/115
213536  9/1987  European Pat. Off. ............ 435/115
8224684 12/1983  Japan .................................... 435/115

OTHER PUBLICATIONS

Lynn et al., in "Amino Acids, Biosynthesis and Genetic Regulation", 1983, pp. 173-177.

*Primary Examiner*—Douglas W. Robinson
*Assistant Examiner*—Irene Marx
*Attorney, Agent, or Firm*—Antonelli, Terry, Stout & Kraus

[57] ABSTRACT

Disclosed is a process for producing L-threonine, which comprises culturing in a medium a microorganism belonging to the genus *Escherichia* and having a resistance to cysteine or cystine, or their analogue and an ability to produce L-threonine until L-threonine is accumulated in the culture broth, and recovering L-threonine therefrom.

9 Claims, No Drawings

PROCESS FOR PRODUCING L-THREONINE

BACKGROUND OF THE INVENTION

The present invention relates to a process for producing L-threonine using a microorganism belonging to the genus Escherichia and having a resistance to cysteine or cystine, or their analogue and an ability to produce L-threonine.

L-threonine is an amino acid which is not only useful as a medicament such as an amino acid preparation, but also utilizable as an additive for animal feed.

Heretofore, various processes for producing L-threonine by fermentation have been known; for example, a process using a microorganism belonging to the genus Escherichia and having a sensitivity to borrelidin (Japanese Published Examined Patent Application No. 6752/76), a process using a microorganism belonging to the genus Escherichia which requires diaminopimelic acid and methionine and of which threonine biosynthesis system is resistant to the feedback inhibition of threonine (Japanese Published Examined Patent Application No. 10037/81), a process using a microorganism belonging to the genus Serratia which is deficient in threonine dehydrogenase and resistant to threonine metabolic antagonist (Japanese Published Examined Patent Application No. 48195/77), a process using a microorganism belonging to the genus Corynebacterium and having a resistance to $\alpha$-amino-$\beta$-hydroxyvaleric acid and S-(2-aminoethyl)-L-cysteine, and a requirement for methionine (Japanese Published Unexamined Patent Application No. 19087/72), a process using a microorganism belonging to the genus Brevibacterium and having a resistance to $\alpha$-amino-$\beta$-hydroxyvaleric acid and S-(2-aminoethyl)-L-cysteine and a requirement for leucine (Japanese Published Unexamined Patent Application No. 31093/75), a process using a microorganism belonging to the genus Brevibacterium and having a resistance to $\alpha$-amino-$\beta$-hydroxyvaleric acid and S-(2-aminoethyl)-L-cysteine and a requirement for L-isoleucine and L-lysine (Japanese Published Unexamined Patent Application No. 224684/83), and a process using a microorganism belonging to the genus Escherichia and having a resistance to at least one of rifampicin, lysine, methionine, aspartic acid and homoserine, or a decreased ability to degrade L-threonine (Japanese Published Unexamined Patent Application No. 273487/88).

SUMMARY OF THE INVENTION

According to the present invention, L-threonine can be produced in high yields by culturing in a medium a microorganism of the genus Escherichia having a resistance to cysteine or cystine, or their analogue and the ability to produce L-threonine until L-threonine is accumulated in the culture broth and recovering L-threonine therefrom.

DETAILED DESCRIPTION OF THE INVENTION

In the process of the present invention, any microorganism may be used so long as it belongs to the genus Escherichia and has a resistance to cysteine or cystine, or their analogue and the ability to produce L-threonine.

Examples of said analogue of cysteine or cystine are S-methylcysteine, S-ethylcysteine, allylglycine, homocysteine, cystine-hydroxamate, cysteic acid, and homocysteic acid.

The mutant strains resistant to cysteine or cystine, or their analogue can be obtained by endowing an L-threonine-producing microorganism of the genus Escherichia with a resistance to cysteine or cystine, or their analogue with a conventional mutation technique.

Examples of the preferable mutant strains are *Escherichia coli* H-7256, *Escherichia coli* H-7263, *Escherichia coli* H-7293 and *Escherichia coli* H-7294.

L-threonine-producing microorganisms belonging to the genus Eschrichia are advantageous for paucity of other amino acids formed as by-products.

A specific example of the procedure for obtaining the above-mentioned mutant strains is given in the following description.

*Escherichia coli* H-4258 (FERM BP-985) which requires diaminopimelic acid and methionine and which is resistant to $\alpha$-amino-$\beta$-hydroxyvaleric acid and rifampicin is treated with 200 $\mu$g/ml N-methyl-N-nitro-N'-nitrosoguanidine (NTG) at 30° C. for 30 minutes.

The treated cells are smeared on a minimum medium [5 g/l glucose, 1 g/l (NH$_4$)$_2$SO$_4$, 2 g/l KH$_2$PO$_4$, 7 g/l K$_2$HPO$_4$, 0.1 g/l MgSO$_4$.7H$_2$O, 20 mg/l Fe$_2$(SO$_4$)$_3$, 50 mg/l diaminopimelic acid, 50 mg/l methionine, and 20 g/l agar, pH 7.2] containing 1 g/l cystine-hydroxamate, and cultured at 30° C. for 2 to 6 days to obtain colonies of cystine-hydroxamate-resistant mutants growable thereon. Then, 50 mutant strains are picked up and subjected to the L-threonine production test. A mutant having a higher L-threonine productivity than that of H-4258 strain is selected. The selected strain has been named *Escherichia coli* H-7256.

Mutants having a resistance to 0.5 g/l allylgylcine, 5 g/l cysteine and 5 g/l cystine, respectively, were prepared in the same manner as above except that allylglycine, cysteine and cystine were respectively used instead of cystine-hydroxamate, and named *Escherichia coli* H-7263, H-7293 and H-7294, respectively.

The strains H-7256, H-7263, H-7293 and H-7294 thus obtained were deposited on November 8, 1988 with the Fermentation Research Institute, Agency of Industrial Science and Technology, Japan under the Budapest Treaty with accession numbers FERM BP-2137, FERM BP-2138, FERM BP-2139 and FERM BP-2140, respectively.

Table 1 shows the growth of the above-mentioned parent strain (H-4258 strain) and the mutant strains when cultured at 30° C. for 24 hours on minimal agar plate media containing cysteine or cystine, or their analogue.

TABLE 1

| | Concentration (g/l) | Growth of strain | | | | |
|---|---|---|---|---|---|---|
| | | H-7256 | H-7263 | H-7293 | H-7294 | H-4258 |
| No addition | 0 | ++ | ++ | ++ | ++ | ++ |
| Cystine-hydroxamate | 0.05 | ++ | — | — | — | — |
| Allylglycine | 0.5 | — | ++ | — | — | — |
| Cysteine | 5 | — | — | ++ | — | — |
| Cystine | 5 | — | — | — | ++ | — |

++: Sufficient growth
—: No growth

L-threonine can be obtained by culturing the above mutants in a synthetic or natural medium containing carbon sources, nitrogen sources, inorganic salts, growth factors and the like until L-threonine is accumulated in the culture broth, and recovering L-threonine therefrom.

As the carbon sources, carbohydrates such as glucose, fructose, molasses, starch hydrolyzate and hydrolyzate of crude sugar, and organic acids such as acetic acid, propionic acid, formic acid, fumaric acid and malic acid, can be used.

As the nitrogen sources, ammonia, ammonium salts of inorganic or organic acids such as ammonium chloride, ammonium sulfate, ammonium acetate and ammonium phosphate, amines and other nitrogen-containing compounds, peptone, meat extract, corn steep liquor, casein hydrolyzate, soybean cake hydrolyzate, various cultured cells and their digest, etc. can be used.

As the inorganic compounds, potassium dihydrogenphosphate, dipotassium hydrogenphosphate, magnesium phosphate, magnesium sulfate, sodium chloride, ferrous sulfate, manganese sulfate, copper sulfate, calcium carbonate, etc. can be used in appropriate amounts.

When the strain used requires nutrients, it is also necessary to add the compounds required for growth to the medium. In some cases, such nutrients may be sufficiently supplied by another medium component and thus specific supplementation is not required.

Culturing is carried out under aerobic conditions, for example, by shaking culture or submerged culture with aeration and agitation at a temperature of 20° to 40° C., preferably 28° to 38° C. The pH of the medium is maintained at 5 to 9, preferably around neutrality during the culturing. The pH is adjusted with calcium carbonate, inorganic or organic acids, alkaline solutions, ammonia, pH buffer solutions, or the like.

Usually, L-threonine is accumulated in the culture broth by culturing for 2 to 7 days. After the completion of culturing, precipitates such as cells are removed from the culture by means of filtration, centrifugation, etc. and L-threonine can be recovered from the resulting broth by combination of ion exchange treatment, concentration, salting-out, etc.

Certain embodiments of the invention are illustrated by the following representative examples.

EXAMPLE 1

*Escherichia coli* H-7256, *Escherichia coli* H-7263, *Escherichia coli* H-7293, *Escherichia coli* H-7294 and *Escherichia coli* H-4258 were used as seed strains. Each strain was cultured with shaking at 30° C. for 16 hours in a seed medium comprising 20 g/l glucose, 10 g/l peptone, 10 g/l yeast extract, 2.5 g/l NaCl and 0.1 g/l diaminopimelic acid. Then 2 ml of the resulting seed culture was inoculated into a 250-ml Erlenmeyer flask containing 20 ml of a fermentation medium having the following composition, and cultured with shaking at 30° C. for 72 hours.

Composition of the fermentation medium: 70 g/l glucose, 14 g/l $(NH_4)_2SO_4$, 2 g/l $KH_2PO_4$, 1 g/l $MgSO_4.7H_2O$, 0.3 g/l diaminopimelic acid, 0.1 g/l DL-methionine, 2 g/l corn steep liquor and 30 g/l $CaCO_3$ (pH 7.4).

The amounts of L-threonine formed in the culture are shown in Table 2.

TABLE 2

| Strain | Property | Amount of L-threonine (g/l) |
|---|---|---|
| H-7256 | Cystine hydroxamate- | 22.3 |

TABLE 2-continued

| Strain | Property | Amount of L-threonine (g/l) |
|---|---|---|
| | resistance | |
| H-7263 | Allylglycine-resistance | 21.2 |
| H-7293 | Cysteine-resistance | 20.1 |
| H-7294 | Cystine-resistance | 19.8 |
| H-4258 | | 17.2 |

The L-threonine-containing fermentation broth obtained by the use of H-7256 strain (200 ml) was subjected to centrifugation (3000 r.p.m., 10 minutes) to remove the cells and other impurities. The obtained supernatant was passed through a column of the strongly acidic cation exchange resin Diaion SKI ($H^+$-type, a product of Mitsubishi Kasei Corporation) to adsorb L-threonine thereon. After the column was washed with water, elution was carried out with 0.5N aqueous ammonia. The fractions containing L-threonine were collected and concentrated, followed by addition of ethanol. The mixture was stored under cooling to give 2.5 g of L-threonine crystals having a purity of 98% or higher.

EXAMPLE 2

Seed culturing of H-7263, H-7293, H-7294 and H-4258 strains was carried out in the same manner as in Example 1. The resulting seed culture (100 ml) was inoculated into a 2-l fermentor containing 1 l of a fermentation medium having the following composition. Culturing was carried out at 30° C. with agitation and aeration (700 r.p.m., 1 l/min) for 80 hours, during which the fermentation medium was appropriately supplied with 60% glucose and the pH of the culture medium was maintained at 6.5 with aqueous ammonia.

Composition of the fermentation medium: 30 g/l glucose, 12 g/l $(NH_4)_2SO_4$, 3 g/l $KH_2PO_4$, 0.2 g/l $MgSO_4.7H_2O$, 6 g/l diaminopimelic acid, 1 g/l DL-methionine and 12 g/l corn steep liquor.

The amounts of L-threonine formed in the culture are shown in Table 3.

TABLE 3

| Strain | Amount of L-threonine (g/l) |
|---|---|
| H-7256 | 63.5 |
| H-7263 | 62.1 |
| H-7293 | 55.8 |
| H-7294 | 56.0 |
| H-4258 | 49.6 |

What is claimed is:

1. A process for producing L-threonine which comprises culturing in a medium a microorganism selected from the group consisting of *Escherichia coli* H-7256 (FERM BP-2137), *Escherichia coli* H-7263 (FERM BP-2138), *Escherichia coli* H-7293 (FERM BP-2139) and *Escherichia coli* H-7294 (FERM BP-2140) which has a resistance to cysteine or cystine, or their analogue and an ability to produce L-threonine until L-threonine is accumulated in the culture broth, and recovering L-threonine therefrom.

2. A process for producing L-threonine which comprises culturing in a medium *Escherichia coli* H-7256 (FERM BP-2137) which has a resistance to cystine hydroxamate and an ability to produce L-threonine until L-threonine is accumulated in the culture broth, and recovering L-threonine therefrom.

3. A process for producing L-threonine which comprises culturing in a medium *Escherichia coli* H-7263 (FERM BP-2138) which has a resistance to allylglycine and an ability to produce L-threonine until L-threonine is accumulated in the culture broth, and recovering L-threonine therefrom.

4. A process for producing L-threonine which comprises culturing in a medium *Escherichia coli* H-7293 (FERM BP-2139) which has a resistance to cysteine and an ability to produce L-threonine until L-threonine is accumulated in the culture broth, and recovering L-threonine therefrom.

5. A process for producing L-threonine which comprises culturing in a medium *Escherichia coli* H-7294 (FERM BP-2140) which has a resistance to cysteine and an ability to produce L-threonine until L-threonine is accumulated in the culture broth, and recovering L-threonine therefrom.

6. A biologically pure culture of *Escherichia coli* H-7256 (FERM BP-2137).

7. A biologically pure culture of *Escherichia coli* H-7263 (FERM BP-2138).

8. A biologically pure culture of *Escherichia coli* H-7293 (FERM BP-2139).

9. A biologically pure culture of *Escherichia coli* H-7294 (FERM BP-2140).

* * * * *